(12) United States Patent
Gingsjo (10) Patent No.: US 8,827,752 B2
(45) Date of Patent: Sep. 9, 2014

(54) SINGLE USE CONNECTION SYSTEM FOR A FETAL ELECTRODE

(75) Inventor: Anders Lars Gingsjo, Kungsbacka (SE)

(73) Assignee: Neoventa Medical AB, Molndal (SE)

( * ) Notice: Subject to any disclaimer, the term of this patent is extended or adjusted under 35 U.S.C. 154(b) by 618 days.

(21) Appl. No.: 13/147,975

(22) PCT Filed: Feb. 5, 2010

(86) PCT No.: PCT/EP2010/000732
§ 371 (c)(1),
(2), (4) Date: Aug. 4, 2011

(87) PCT Pub. No.: WO2010/089134
PCT Pub. Date: Aug. 12, 2010

(65) Prior Publication Data
US 2011/0294360 A1    Dec. 1, 2011

(30) Foreign Application Priority Data
Feb. 6, 2009    (GB) .................................... 0902071.0

(51) Int. Cl.
| | | |
|---|---|---|
| *H01R 24/04* | (2006.01) | |
| *A61B 5/024* | (2006.01) | |
| *H01R 9/03* | (2006.01) | |
| *A61B 5/0448* | (2006.01) | |
| *A61B 5/00* | (2006.01) | |
| *H01R 24/58* | (2011.01) | |
| *H01R 103/00* | (2006.01) | |

(52) U.S. Cl.
CPC ......... *A61B 5/0448* (2013.01); *A61B 2562/227* (2013.01); *A61B 5/02411* (2013.01); *A61B 2562/226* (2013.01); *H01R 9/03* (2013.01); *H01R 2201/12* (2013.01); *H01R 2103/00* (2013.01); *A61B 5/4362* (2013.01); *H01R 24/58* (2013.01); *Y10S 439/909* (2013.01)
USPC .......................................... 439/669; 439/909

(58) Field of Classification Search
USPC ........................... 439/668, 669, 607, 909, 955
See application file for complete search history.

(56) References Cited

U.S. PATENT DOCUMENTS

| | | |
|---|---|---|
| 3,827,428 A | 8/1974 | Hon et al. |
| 3,911,906 A | 10/1975 | Reinhold, Jr. |

(Continued)

FOREIGN PATENT DOCUMENTS

| | | |
|---|---|---|
| EP | 1 738 686 A1 | 3/2007 |
| WO | 2005/034744 A2 | 4/2005 |
| WO | 2008068695 A1 | 6/2008 |

OTHER PUBLICATIONS

International Search Report for Serial No. PCT/EP2010/000732 dated May 5, 2010.

(Continued)

*Primary Examiner* — Phuong Dinh
(74) *Attorney, Agent, or Firm* — McCormick, Paulding & Huber LLP (57) ABSTRACT

A single-use connector (1) for a fetal electrode is provided. The housing (10) of the connector is molded together as two shells (10a, 10b) of substantially rigid material where each shell is integrally connected to the other along a common straight portion of edge (12). This provides the housing with a clam-shell form. The housing is also provided with a socket (11) for receiving a plug (2) of a fetal electrode. The plug is provided with two or more electrical contacts (23, 24) to feed electrical signals from the fetal electrode.

16 Claims, 10 Drawing Sheets

(56) References Cited

U.S. PATENT DOCUMENTS

| | | | |
|---|---|---|---|
| 4,209,020 A | 6/1980 | Nielsen | |
| 4,632,121 A * | 12/1986 | Johnson et al. | 600/372 |
| 4,963,103 A | 10/1990 | Fink et al. | |
| 5,046,965 A | 9/1991 | Neese et al. | |
| 5,062,426 A | 11/1991 | Ulbrich et al. | |
| 5,168,876 A * | 12/1992 | Quedens et al. | 600/376 |
| 5,197,472 A | 3/1993 | DiSabito | |
| 5,199,432 A | 4/1993 | Quedens et al. | |
| 5,205,288 A * | 4/1993 | Quedens et al. | 600/376 |
| 5,404,876 A | 4/1995 | DiSabito et al. | |
| 6,321,103 B1 | 11/2001 | Dowd et al. | |
| 6,325,671 B1 | 12/2001 | Radliff | |
| 6,356,778 B1 * | 3/2002 | Pirc | 600/376 |
| 6,363,272 B1 | 3/2002 | Combs | |
| 7,336,985 B2 | 2/2008 | Wallace et al. | |

OTHER PUBLICATIONS

Search Report for GB Serial No. GB0902071.0 dated May 18, 2009.
Search Report for GB Serial No. 1001979.2 dated May 29, 2010.
Examination Report for GB Serial No. 1001979.2 dated Mar. 31, 2011.

* cited by examiner

SINGLE USE CONNECTION SYSTEM FOR A FETAL ELECTRODE

CROSS REFERENCE TO RELATED APPLICATIONS

This application is entitled to the benefit of and incorporates by reference essential subject matter disclosed in International Patent Application No. PCT/EP2010/000732 filed on Feb. 5, 2010 and Great Britain Patent Application No. 0902071.0 filed Feb. 6, 2009.

FIELD OF THE INVENTION

The present invention relates to a single-use connection system for a fetal electrode, for example, a single-use connector for use with a fetal scalp electrode and a connector assembly adapted to ensure single use. There is also provided a method of manufacturing the single-use connector.

BACKGROUND OF THE INVENTION

During some births it becomes necessary to monitor the fetal heart rate. A fetal electrode, such as the one illustrated in U.S. Pat. No. 3,827,428, is attached to the scalp of the fetus and a pair of leads is passed back through the birth canal to a connector strapped to the mother's leg, hence these connectors are usually referred to as "leg-plate" connectors. An additional electrode from the leg-plate connector is attached to the mother to establish a base or reference potential for the electrical signals of the fetal electrode. The electrical signals from the fetal electrode and the reference electrode are then fed to a fetal monitor via leads extending from the leg-plate connector.

Examples of conventional leg-plate connectors are illustrated in U.S. Pat. No. 5,199,432, U.S. Pat. No. 6,321,103, U.S. Pat. No. 6,363,272 and US-A-2005137486. In these arrangements, the leg-plate connector can be re-used. They are provided with a socket for receiving an elongate plug attached to the ends of the electrode wires. Due to the presence of bodily fluids, however, there is a significant health risk of cross-contamination, for example, where leg-plate connectors are not adequately cleaned and sterilised before they are reused. Many developments have been made to try to minimise the ingress of bodily fluids and to resist the aggressive antiseptic detergents, for example the inclusion of O-ring seals and the use of special materials, but these have also lead to complicated manufacturing processes and high production costs.

As a result, moves have been made to develop single-use, disposable, leg-plate connectors, which can benefit from a more simplified construction and reduced cost. Examples are shown in U.S. Pat. No. 4,209,020, U.S. Pat. No. 5,062,426, U.S. Pat. No. 5,197,472 and U.S. Pat. No. 5,404,876. One recognised advantage of disposable leg-plate connectors is that they can be made lighter and have a lower profile, and this leads to improved comfort for the wearer and improvements to the quality of the fetal ECG signal. In order to make these disposable leg-plate connectors as thin as possible, the wires from the fetal electrode were fed individually as bare wires into a terminal, in order to make an electrical contact. The use of such bare wires is no longer allowed for leg-plate connectors.

A problem with these thin, single-use, leg-plate connectors is that while they offer some advantages, they have not been optimised for use by the person fitting the device, e.g., the midwife. The flexible electrode wires are small and can be difficult to connect up, particularly in the presence of bodily fluids. It is paramount that a good connection is made with the ends of the fetal electrode leads, otherwise there is a reduction in the signal quality. It is also important to obtain a good signal from the material reference electrode positioned under the connector.

It would also be desirable to provide a method of manufacturing such a connector that is straight forward and low cost.

There is also a problem that the current single-use connector systems do not prevent re-use.

SUMMARY OF THE INVENTION

According to a first aspect of the present invention, there is provided a single-use connector for a fetal electrode, the connector comprising:

a housing having a first socket for receiving a plug of a fetal electrode;

two or more contacts arranged within the first socket for receiving electrical signals from the plug when it is inserted;

a second socket for a maternal reference electrode provided on an underside of the housing, wherein the housing is made from a moulded body which has a clam-shell form, the housing comprising two shells of substantially rigid material providing, in use, the underside and a top surface of the housing respectively, where each shell is integrally connected to the other along a common straight portion of edge.

Thus, the disposable, single-use connector is optimised for use by the person fitting the device, because the housing includes a first socket, which is an electrical socket for a plug connected to the ends of the electrical leads of the fetal electrode. The single plug resembles a phono jack of a stereo audio system, and is consequently large enough to be gripped and manipulated easily in a slippery environment, making connection to the connector simple. The clam-shell construction of the housing provides three dimensional form to facilitate ease of handling by the midwife and to accommodate the first and second sockets.

The plug may be elongate, and have a handle portion for gripping by the midwife and a contact portion that is adapted to be received within the first socket in a form fitting way. The contact portion of the plug may also be provided with recessed contact regions that engage with sprung contact elements of the connector, providing the midwife with positive feedback that a proper connection has been established when the plug is pushed home. A conical entrance to the first socket may be provided to help seal the connection between the plug and the connector.

The clam-shell form of the housing, as well as providing the three dimensional form required for receiving the plug, also provides a number of advantages from a manufacturing point of view.

Firstly, the housing can be moulded in an open configuration between two dies of a moulding apparatus, so that one die of the moulding apparatus forms the interior surface of both shells of the housing, and the other die forms the exterior surface of the shells. This is advantageous because like features of each shell are formed by the same die. Consequently the moulding operation can be optimised for any differences in cooling rates or finish required for the interior or exterior surfaces. Since the die surface will tend to wear over time with use, and there may be differences in the rate of wear for the two dies, the clam-shell form of the housing means that this will not lead to differences in the surface finish between the top and underside surfaces. Thus the dies can be replaced at different times as necessary. The moulded blanks or bodies are also easier to handle by the machinery because the shells are already connected together by the integral connection along the straight edge portion which is common to both shells. This common edge portion forms a hinge, about which the shells can be closed. Alignment of the shells into a closed configuration in order to join the remainder of the shell perimeters is also easier because the two shells are already pre-aligned through the hinge.

Thus, viewed from another aspect, there is provided a method of making a single-use connector for a fetal electrode comprising the steps of:

moulding a housing of the connector by providing material between opposed die faces of a moulding apparatus, the housing being moulded in an open configuration where one die face provides the internal surface profile of the housing and the other die face provides the external surface profile of the housing, whereby the moulded housing has a clam-shell form comprising two shells of substantially rigid material that are integrally connected along a common straight portion of edge which hinges the shells together;

closing the moulded housing so that a remainder of the edges of the shells are brought together; and fastening the shells together to retain the shells in a closed configuration.

Preferably the shells of the housing are substantially triangular in outline, for example, having a rounded triangular perimeter. This shape can minimise the amount of material required to form the leg-plate connector. Each shell preferably has two edges extending at roughly 90° to each other that are of the same or nearly the same length, and having a third, longer edge extending at roughly 45° to the other two shorter edges. In other words, preferably each shell has a substantially right angle triangular outline, preferably with rounded corners. The longer edge may be around 1.4 times the length of the two shorter edges. The longer edge preferably includes the hinge connecting the two shells of the housing.

An advantage of making the shells this shape is that, during moulding, a square (or possibly a rectangular or parallelepiped) blank of material can be used, with the hinge extending along the diagonal of the blank. This helps to avoid waste during the manufacturing process and makes the blanks easier to handle.

In another embodiment, the material of the housing is provided by injecting material between the opposed dies of the moulding apparatus.

Other shapes are also possible for the clam-shell form of the housing. The housing could have a square or rectangular profile, a pentagonal, hexagonal or other polygonal profile, or a curved profile, with the various profiles having a straight edge where the shells are hinged together.

The remainder of the edge may be fastened together by any means. Preferably the opposing edges of the shells are welded together. They could also be joined by adhesive. In an alternative arrangement a mechanical fastening could be provided, for example a male connector portion on one shell which engages and locks into a female connector portion on the other shell.

The housing is preferably moulded from plastics, though any cheap, lightweight, easily mouldable material, which is also an electrical insulator, could be used.

Since the connector, which is optimised for single use, can be made much lighter than the reusable connectors, the connector is much more comfortable for the mother. It can also be made to a less complicated design, reducing manufacturing costs. Thus, the connector is adapted to be disposable. For example, stiff O-ring seals for sealing around the connector plug and the cable exit to the fetal monitor are no longer needed. Consequently the connector may be characterised by an absence of such O-ring seals. The need for ports and other features to be flush for cleaning, or the provision of materials that are washable with aggressive antiseptic detergents, is also no longer necessary, because it is a single use connector. The connector may therefore have a surface profile which is not smooth or may not include ports for flushing the connector with disinfectant fluids. The connector can also be provided with more flexible and lighter wires for connecting to the fetal monitor than compared with a traditional multiuse connector, thereby further improving the comfort for the mother during labour. The advantages of such a single-use, light and ductile leg-plate connector are not only ergonomic, e.g., it is more comfortable for the mother, easier to place, etc., there is also less risk of microbial contamination between patients.

Furthermore, from a signal quality perspective, a lighter leg-plate connector with more flexible wires will lead to less relative movement of the maternal reference electrode, and hence less movement at the maternal-skin electrode interface, leading to less baseline interference in the fetal ECG signal.

In contrast to known disposable leg-plate connectors that are currently available, or the smooth surface profiles of the re-usable connectors, preferably the connector of the present invention includes an abrasive surface for abrading the skin of the mother prior to attachment of the maternal reference electrode. The maternal reference electrode is preferably in the form of a self-adhesive maternal-skin electrode, and preferably serves the function of holding the connector in place on the leg of the mother. In order to obtain a low impedance connection to the skin, the dry top layer of the skin should be removed first. Normally this is done by sandpapering the area where the skin electrode is to be applied. However, with a single-use leg-plate connector, where cleaning of the connector between patients is not an issue, an abrasive surface can be added to the connector. The prior art single-use connectors would be too thin, and hence too flexible, to incorporate such an abrasive surface. Providing the abrasive surface on the connector itself means that it is much easier to locate during the active environment of the delivery room than, for example, a loose piece of sandpaper, and there is the added benefit that it can be sterilised during the manufacturing and packaging process of the connector.

In the present invention, the three dimensional form provided by the pair of substantially rigid shells allows the connector to be gripped easily by the midwife and for pressure to be applied against the skin of the mother while the abrasive surface of the connector is rubbed against the mother's skin. The preferred triangular profile of the connector shells with a long straight edge, in particular, assists with this, allowing the connector to be held pinched between finger and thumb and used as a scraper on the mother's skin. The provision of the abrasive surface along the long edge means that a wide region of dry skin corresponding to the area required by the maternal-skin electrode, can be abraded easily by the midwife.

Viewed from a further aspect, the present invention provides a single-use connector for a fetal electrode comprising a housing which is provided with an abrasive surface for abrading a region of the maternal skin prior to attachment of a maternal-skin electrode. The connector may have any or all of the features already described above, for example: a first socket for receiving a plug of a fetal electrode, two or more contacts arranged within the first socket for receiving electrical signals from the plug when it is inserted, a second socket for a maternal reference electrode provided on an underside of the housing, and/or the housing may be made from a moulded body which has a clamshell form, the housing comprising two shells of substantially rigid material providing, in use, the underside and a top surface of the housing respectively, where each shell is integrally connected to the other along a common straight portion of edge.

The abrasive surface may be integral with the housing. It could be formed by providing a series of small sharp projections, for example, teeth or ridges, on the external surface of the connector, for example, during moulding. In one embodiment, an edge of the connector containing the hinge, for example, the long edge, has a rounded-convex profile extending between the underside and top surface, and the abrasive surface is provided around this convex edge. The sharpness is naturally limited by the moulding of the plastic material which stops the ridges from being too sharp. Preferably the ridges are straight and extend in a direction which is parallel or substantially parallel to the hinge axis. The projections may all have the same profile or a region may vary to provide a different level of abrasion.

In another arrangement, an abrasive material is applied to a portion of the connector housing. The abrasive surface may consist of a strip of sand-paper, or strips of sand-paper, preferably of different grades, e.g., a rough and a smoother grade, which is attached with adhesive. Alternatively the abrasive surface may be a coating applied to a selected region that contains abrasive particles within a retaining matrix.

In one arrangement the abrasive surface has (or has the equivalent of) a 240 to 800 grit sandpaper, more preferably a fine grit of the order of around 400. The abrasive surface may be located in a shallow recess of the housing.

In some embodiments, the maternal-skin electrode may be detachable from the second socket in the connector so that it can be removed prior to abrading the mother's skin and then refitted on the connector before the electrode and connector assembly is attached to the mother's leg. The maternal-skin electrode may include a protrusion that plugs into the second socket of the connector to engage an electrical contact member within the housing.

Within the housing are provided contact members for the fetal electrode plug and for the maternal-skin electrode. Preferably these contact members are formed from the same base geometry in order to reduce manufacturing overheads. In one embodiment the contact members have a crook profile, with the contact member of the maternal-skin electrode having a longer circumferential portion than the plug contact members. In the case of each of the contact members for the fetal electrode plug, the circumferential portion may provide a sprung contact element that projects into the first socket to engage a contact on the plug. A solder-free connection, for example a crimped connection, may be provided between the contact members and any electrical wires leading to a monitoring device, to simplify the manufacturing further.

The manufacturing advantages of making the contact members from the same base geometry are obtained independently of the other preferred features such as the clam-shell form. Therefore, according to a further aspect there is provided a single-use connector for a fetal electrode, the connector comprising:

a housing having a first socket for receiving a plug of a fetal electrode;

two or more contacts arranged within the first socket for receiving electrical signals from the plug when it is inserted;

a second socket for a maternal reference electrode provided on an underside of the housing, the second socket having a contact for receiving electrical signals from the maternal reference electrode when connected thereto, wherein within the housing there are arranged at least three contact members providing the contacts for the first and second sockets, the at least three contact members being formed of the same base geometry and each having a crook profile.

The method of the present invention may also include the step of forming a strip of metal into a crook profile, cutting the profiled strip into a set of contact members, and arranging the set of contact members within the housing of the connector.

The connector of the present invention is intended to be a single-use only item, and hence disposed after the use. In order to prevent multiple use, and transmission of infectious diseases, the connector may be fitted with a programmable electronic ID-device, for example, in the form of an ID-chip located within the housing of the connector. Preferably the programmable electronic ID-device is electrically connected to one of the contacts provided within the connector using a solderless electrical connection. In one embodiment, the fetal monitor labels the ID-device with a date and time upon connection. The fetal monitor then accepts the connector for a limited amount of time only.

Thus viewed from another aspect, the present invention provides a single-use connector for a fetal electrode, the connector including a programmable electronic ID-device which is adapted to prevent re-use, for example, by limiting the amount of time that the connector can be used for.

The connector may have any or all of the features already described above, for example: a first socket for receiving a plug of a fetal electrode, two or more contacts arranged within the first socket for receiving electrical signals from the plug when it is inserted, a second socket for a maternal reference electrode provided on an underside of the housing, and/or a housing that is made from a moulded body which has a clamshell form, the housing comprising two shells of substantially rigid material providing, in use, the underside and a top surface of the housing respectively, where each shell is integrally connected to the other along a common straight portion of edge.

The connector is intended for use in a single-use connection system for a fetal electrode. Thus viewed from another broad aspect, the present invention provides a single-use connection system for a fetal electrode, comprising:

a fetal electrode, with leads extending therefrom for conveying signals from the fetal electrode;

a disposable connector, adapted for mounting onto a leg, the connector having means for connecting the leads from the fetal electrode, the connector further having means for connecting a maternal reference electrode;

leads extending from the connector for conveying the signals to a fetal monitor, wherein the leads from the fetal electrode are fitted with a plug and the connector comprises a housing which is provided with a socket for receiving the plug. Preferably the housing comprises two substantially triangular shells joined together to define an underside and a top surface of the housing, wherein an opening for the plug socket is provided in an edge surface at a corner of the housing and the plug socket extends along one edge of the housing spaced away from a second socket for a maternal reference electrode.

The programmable electronic ID-device may be provided in another of the components making up the fetal electrode system, for example, in any one of: the fetal electrode, the plug connected to the fetal electrode, an intermediary component positioned between the fetal electrode and the plug, the connector, a plug on the connector leads that plugs into a fetal monitor or an adapter leading to a fetal monitor, or an intermediary component positioned along such leads from the connector. Thus a single-use connection system for a fetal electrode in accordance with the present invention can be seen to comprise a set of components, some of which may be irremovably joined together, including a fetal electrode, fetal electrode leads, a plug for the fetal electrode, a connector, a maternal reference electrode, connector leads and a plug fitted to those leads, wherein at least one of the components is fitted with a programmable electronic ID-device which limits the amount of time that the set can be used for or in some other way prevents re-use of the disposable components. For example, a connector assembly comprising the connector, an irremovable set of leads leading from the connector and a plug irremovably fitted to the leads, may be provided with a programmable electronic ID-device. In one arrangement this is provided in the connector, but preferably it is housed in the connector plug.

The connector leads may be housed within a common protective sleeve, which forms a single cable, leading to the connector plug. In one preferred arrangement, the present invention provides a connector assembly comprising a connector for a fetal electrode, for example as described above, a cable extending from the connector which comprises leads for conveying electrical signals from the connector to a fetal monitor, the cable terminating in a connector plug, wherein the connector plug contains a programmable electronic ID-device that is adapted to prevent re-use of the connector.

This arrangement is most preferred because an electronic ID-device can be easily incorporated into the connector plug during the manufacturing process and avoids the need for additional leads, reducing manufacturing costs further. The connector may have any or all of the features already described above, for example: a first socket for receiving a plug of a fetal electrode, two or more contacts arranged within the first socket for receiving electrical signals from the plug when it is inserted, a second socket for a maternal reference electrode provided on an underside of the housing, and/or a housing that is made from a moulded body which has a clamshell form, the housing comprising two shells of substantially rigid material providing, in use, the underside and a top surface of the housing respectively, where each shell is integrally connected to the other along a common straight portion of edge.

The connector plug could be any conventional plug, but is preferably an eight position eight contact plug such as an RJ-45 plug (which is a plug often used for Ethernet data cables). These are commonly available plugs, which means that tooling for fitting the plugs is also readily available and so this reduces the cost of the single-use connector assembly further. However, a problem arises because sockets for these plugs can be found on many types of device, for example network devices with Ethernet connectivity, and there is a risk that the connector plug may be inadvertently plugged into the wrong piece of equipment, leading to possible electrical shock of the mother or fetus. Therefore, preferably the RJ-45 connector plug includes a blocking member that projects from a surface of the connector plug to block the insertion of the connector plug into a standard, unmodified RJ-45 socket. In other words, the RJ-45 connector plug is adapted so that it can only be plugged into a correspondingly adapted RJ-45 socket in the fetal monitor or adapter leading to the monitor. The benefits of the reduced production costs are achieved independently of the other preferred features described above, though most preferably, this modified RJ-45 connector plug is used in conjunction with any or all of the features previously described.

Thus viewed from a further aspect the present invention can be seen to encompass a connector assembly comprising a connector for a fetal electrode which is irremovably attached to one end of a cable, and a connector plug which is irremovably attached to the other end of the cable, wherein the connector plug is an RJ-45 format plug which has been adapted to include a blocking member that projects from a surface of the connector plug to block the insertion of the connector plug in a standard, unmodified RJ-45 socket. Preferably the connector for the fetal electrode is a disposable connector of the type previously described having a moulded clam-shell form and preferably an abrasive surface. Also preferably the RJ-45 format connector plug includes a programmable electronic ID-device which prevent the re-use of the connector assembly on another person.

In preferred embodiments, the blocking member that projects from a surface of the connector plug comprises a pin that is retained protruding from a hole in the connector plug, wherein an end of the pin that is retained within the connector plug is provided with a recess, and during crimping of electrical connections to the connector plug, the pin is locked in place through engagement of an electrical contact of the connector plug with the recess in the pin. This provides the advantage that the connector plug can be modified with the additional blocking member during the crimping operation that connects the electrical contacts to the individual leads within the cable.

In another embodiment the fetal electrode itself is provided with a programmable electronic ID-device. Such ID-devices are available which require only one extra connection or wire apart from the ground connector or wire. They are small enough (less than 4 mm) to be located within the cylindrical hub of a fetal electrode.

The fetal monitor, or an adapter between the monitor and the connector assembly, can be set up to only accept certain types of connector and/or fetal electrode, thereby ensuring that only safe components of the highest quality are used.

BRIEF DESCRIPTION OF THE DRAWINGS

Certain preferred embodiments of the present invention will now be described in further detail by way of example only and with reference to the accompanying drawings, in which.

DETAILED DESCRIPTION OF THE PREFERRED EMBODIMENTS

Figure 1:
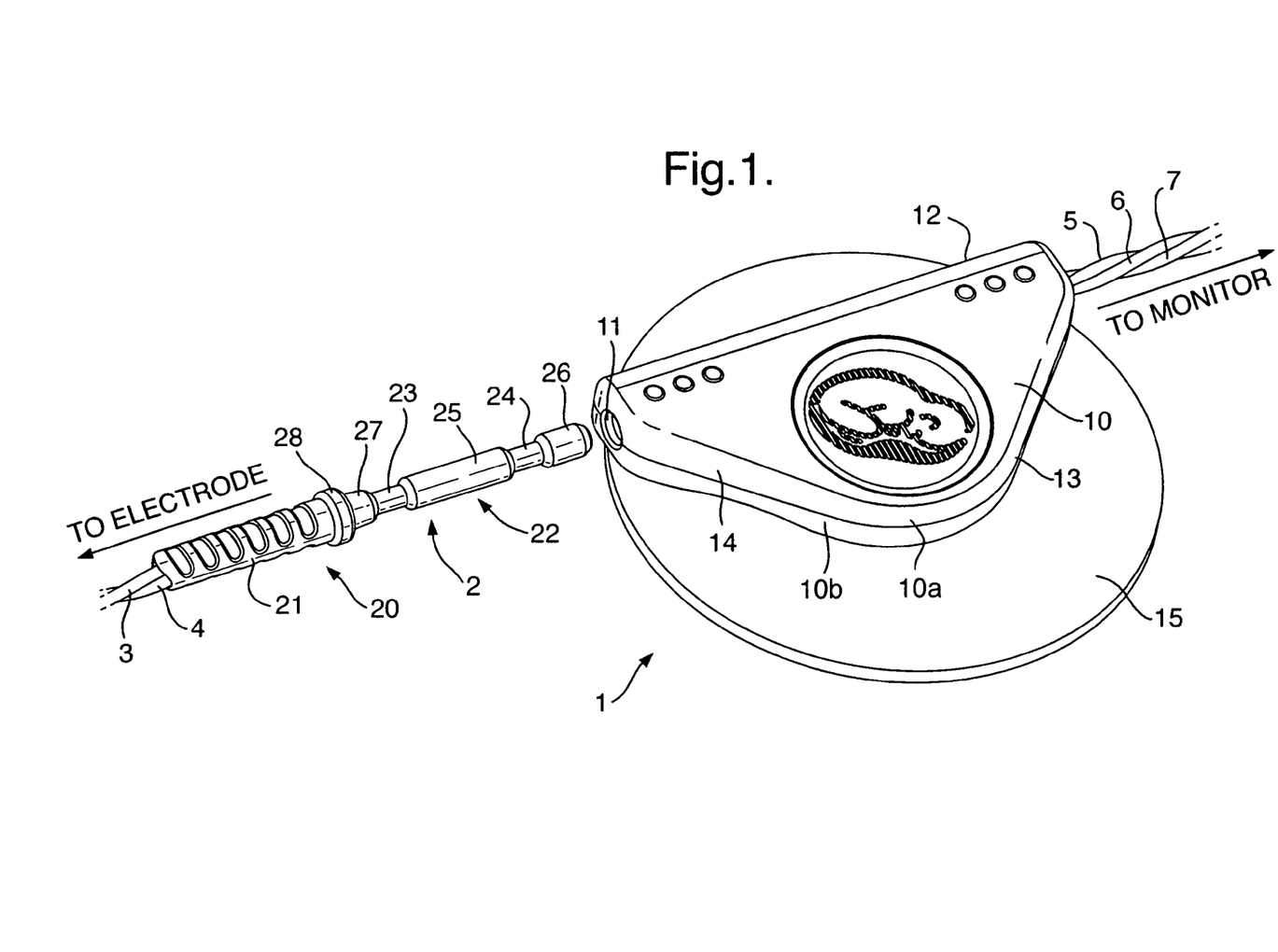
FIG. 1 is a perspective view of a preferred embodiment of a leg-plate connector according to the present invention.

FIG. 1 shows a perspective view of a preferred embodiment of the leg-plate connector 1, which feeds the electrical signals from a fetal electrode (not shown) to a fetal monitor (also not shown). The leg-plate connector 1 comprises a housing 10 which is provided with a first socket 11 for receiving a plug 2 fitted to the ends of the electrical leads 3, 4 coming from the fetal electrode. At the opposite end of the housing 10 to the first socket 11, three electrical leads 5, 6, 7 exit the housing 10 and convey electrical signals to the fetal monitor.

The housing 10 is made from two halves or shells 10a, 10b, moulded from plastics, which have a substantially triangular shape. Each shell 10a, 10b has a long edge 12 forming the hypotenuse and two smaller edges 13, 14, providing the opposite and adjacent sides of a substantially right angle triangle with rounded corners.

Connected to the underside shell 10b of the housing 10, is a maternal-skin electrode 15 to provide a reference potential for the ECG signal. The maternal-skin electrode 15 can be unplugged from the housing 10 and may include an adhesive layer for fastening the electrode to the mother's skin. The maternal-skin electrode 15 is preferably circular, as shown.

As can be seen from FIG. 1, the maternal-skin electrode 15 plugs into the underside shell 10b close to the right-angled corner of the housing, while the first socket 11 and the electrical leads 5, 6, 7 to the fetal monitor are provided in and extend from the other two acute corners of the housing 10. In other words, the connection to the maternal-skin electrode 15 is spaced away from the line of the socket 11.

The plug 2, which is fitted to the end of the fetal electrode leads 3, 4, is an elongate device having a grip portion 20 for the midwife to hold and includes a flexible region 21 that is arranged to grip and support the electrode leads 3, 4 as they exit from one end of the plug 2. Beyond the grip portion 20 there is provided a contact portion 22 which is sized to fit within the first socket 11 of the housing 10. The contact portion 22 includes a first electrical contact 23 and a second electrical contact 24 for conveying the electrical signals from the fetal electrode. The electrical contacts 23, 24 are a cylindrical shape and separated axially by a cylindrical spacer 25 of an insulating material. Further cylindrical elements of insulation form the plug tip 26 and plug neck 27. The plug neck 27 is conical in section to seal against a corresponding conical mouth portion of the first socket 11. The contact portion 22, comprising first and second electrical contacts 23, 24, the cylindrical spacer 25, plug tip 26 and plug neck 27, is separated from the grip portion 20 by a collar 28, which provides a stop that abuts against the housing 10 when the contact portion 22 of the plug 2 has been fully inserted within the first socket 11.

Figure 2A:
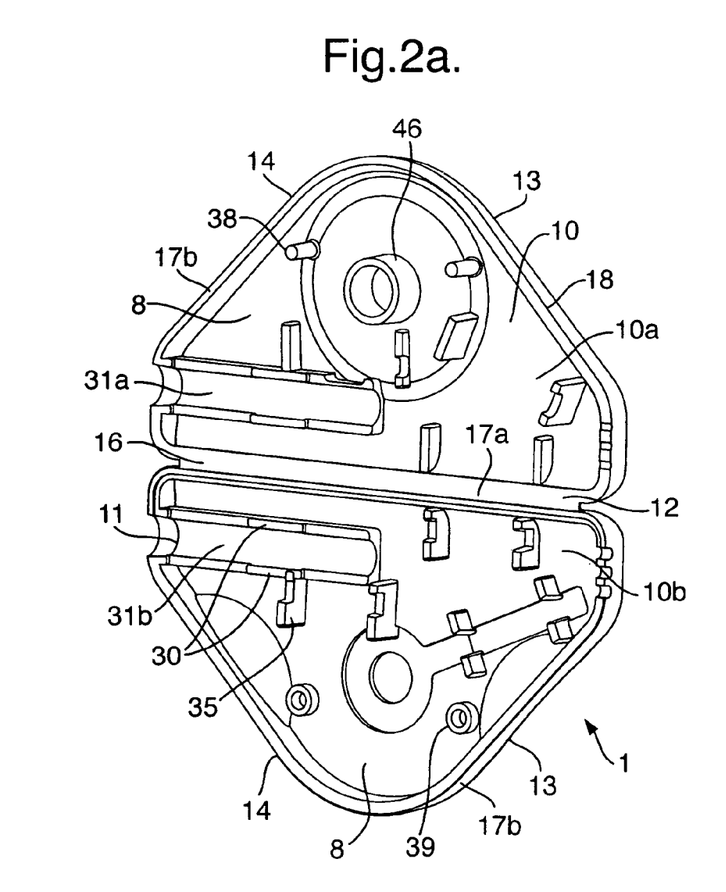
FIGS. 2a and 2b illustrate perspective views of the interior and exterior of the connector of FIG. 1 in an open configuration.

FIG. 2a shows a perspective view of the interior surface 8 of the two shells 10a, 10b forming the leg-plate connector 1. The clam-shell form of the housing 10 can be clearly seen. Each shell 10a, 10b has a substantially right angle triangular shape, having two short edges 13, 14 and a long edge 12 which is common to both shells 10a and 10b. A hinge 16 is formed by a tongue of material that joins the top side of the housing 10a to the underside of the housing 10b along the long edge 12. The shells 10a and 10b are integrally connected by this hinge 16.

As can be seen from FIG. 2a, the two shells 10a, 10b are each provided with an encircling edge section 17a and 17b, that defines a perimeter 18 of each shell 10a, 10b. The shells 10a, 10b are integrally connected with each other along the common straight portion 12 of each shell's perimeter 18 to form a hinged edge region 17a. During a subsequent processing step, the shells 10a, 10b are closed together and the remainder of each perimeter 18 is welded together where each touch to form joined edge region or regions 17b. The edge region 17b may be continuous for the entire remainder of the perimeter 18 or may only be joined only in places sufficient to retain the shells 10a, 10b in a closed configuration.

Moulded within the internal surface 8 is a pair of ribs 30 which form the extremities of a semi-cylindrical recess 31b providing one half of the first socket 11. The other half of the first socket 11 is formed by a corresponding semi-cylindrical recess 31a moulded into the interior surface 8 of the top side of the housing 10a through a corresponding pair of ribs 30.

Figure 3:
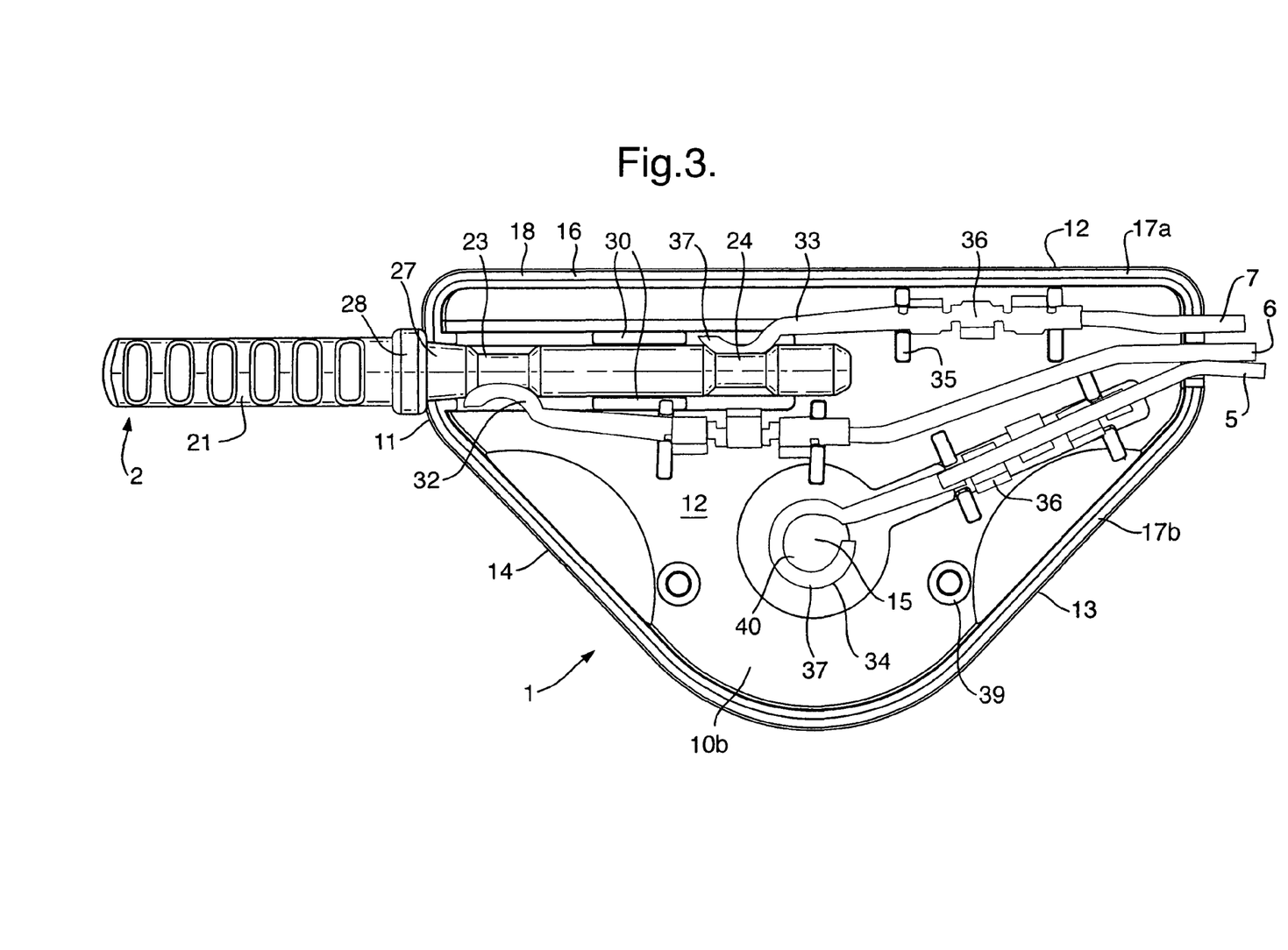
FIG. 3 shows an enlarged perspective view of the interior of one half of the connector, showing how the fetal electrode plug connects up with the wires leading to the fetal monitor.

Gaps in these ribs 30 provide access for a first electrical contact member 32 to urge against first contact 23 of plug 2, and second electrical contact member 33 to urge against second contact 24 (see FIG. 3). A third electrical contact member 34 is provided for urging against contact portion 40 of the maternal-skin electrode 15. The first, second and third electrical contact members 32, 33, 34 are held in place by locating members 35 moulded on the interior surface 8.

The contact members 32, 33, 34 have the same base geometry, and comprise a substantially straight section 36, which grips the end of a wire 5, 6, 7 and is held in place between two pairs of locating members 35, and a curved circumferential portion 37, which makes electrical contact with the plug 2 or the maternal-skin electrode 15. In the case of the first and second electrical contact members 32, 33, the circumferential portion 37 acts as a sprung contact to urge against the first contact 23 and second contact 24 of plug 2, respectively. As seen from FIG. 3, the circumferential portion 37 of the third electrical contact member 34 is of the same radius as the circumferential portions 37 of the first and second electrical contact members 32, 33, but is longer in order to substantially encircle and grip the contact portion 40 of the maternal-skin electrode 15. The electrical contact members 32, 33, 34 are provided with gripping elements to avoid the need for a solder connection to the wires 5, 6, 7.

To help align and retain the shells 10a, 10b in a closed configuration, pegs 38 are provided extending from one of the shells 10a, 10b to engage in a locking manner with corresponding cups 39 in the other of the shells 10a, 10b. The pegs 38 and cups 39 may provide sufficient locking force that it is not necessary to weld, or join with adhesive, the edge regions 17b of the shells 10a and 10b. Additional pegs 38 and cups 39 may be positioned as necessary to achieve this.

In order to obtain a low impedance connection to the skin, the dry top layer of skin should be removed. Normally this is done by sandpapering the area where the maternal-skin electrode 15 is to be applied. With a single-use leg-plate connector 1, where cleaning between patients is not an issue, an abrasive surface 41 can be added to the housing 10. This is shown in FIGS. 4a and 4b, which illustrate perspective views of the assembled connector 1 with the two shells 10a, 10b joined together in a closed configuration.

Figure 4A:
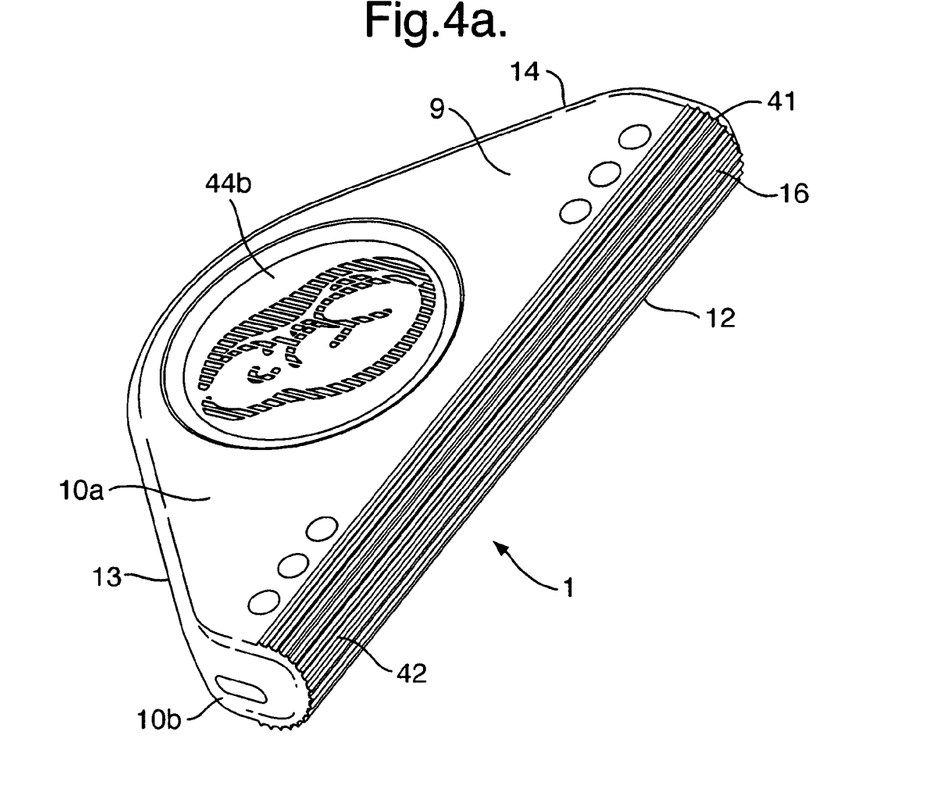
FIGS. 4a and 4b are perspective views of the exterior of the connector of FIGS. 2a and 2b when it is in a closed configuration.
Figure 4B:
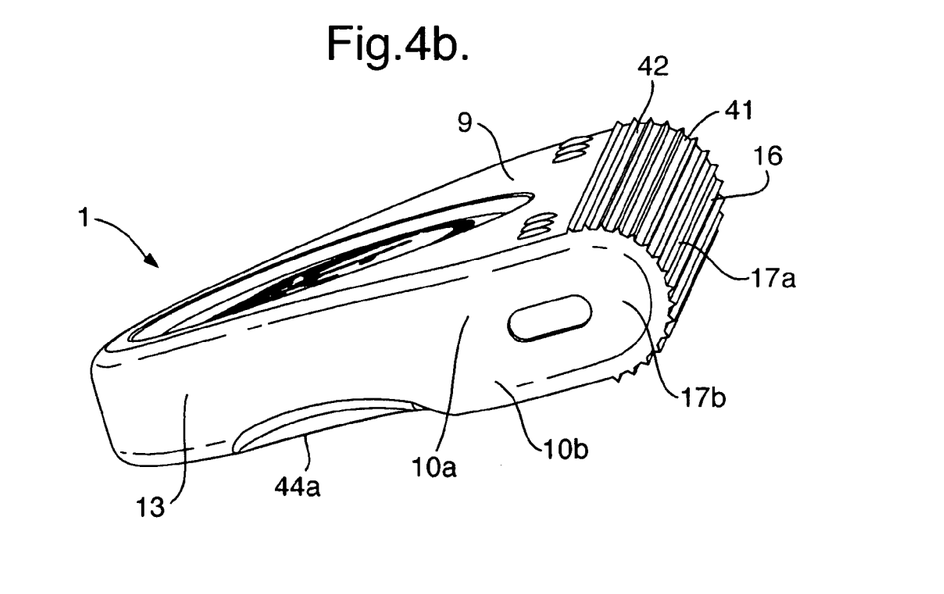

Thus in FIGS. 4a and 4b, it can be seen that the long edge 12 of the housing 10 is straight in the direction of the hinge 16, but it is also rounded off when viewed edge on to give a semi-cylindrical profile. On this rounded long edge 12 an abrasive surface 41 for abrading the mother's leg prior to application of the maternal-skin electrode 15 is provided. In the embodiment of FIGS. 4a and 4b, the abrasive surface 41 is formed by an array of ridges 42 that are arranged parallel to the axis of the hinge 16.

Figure 5:
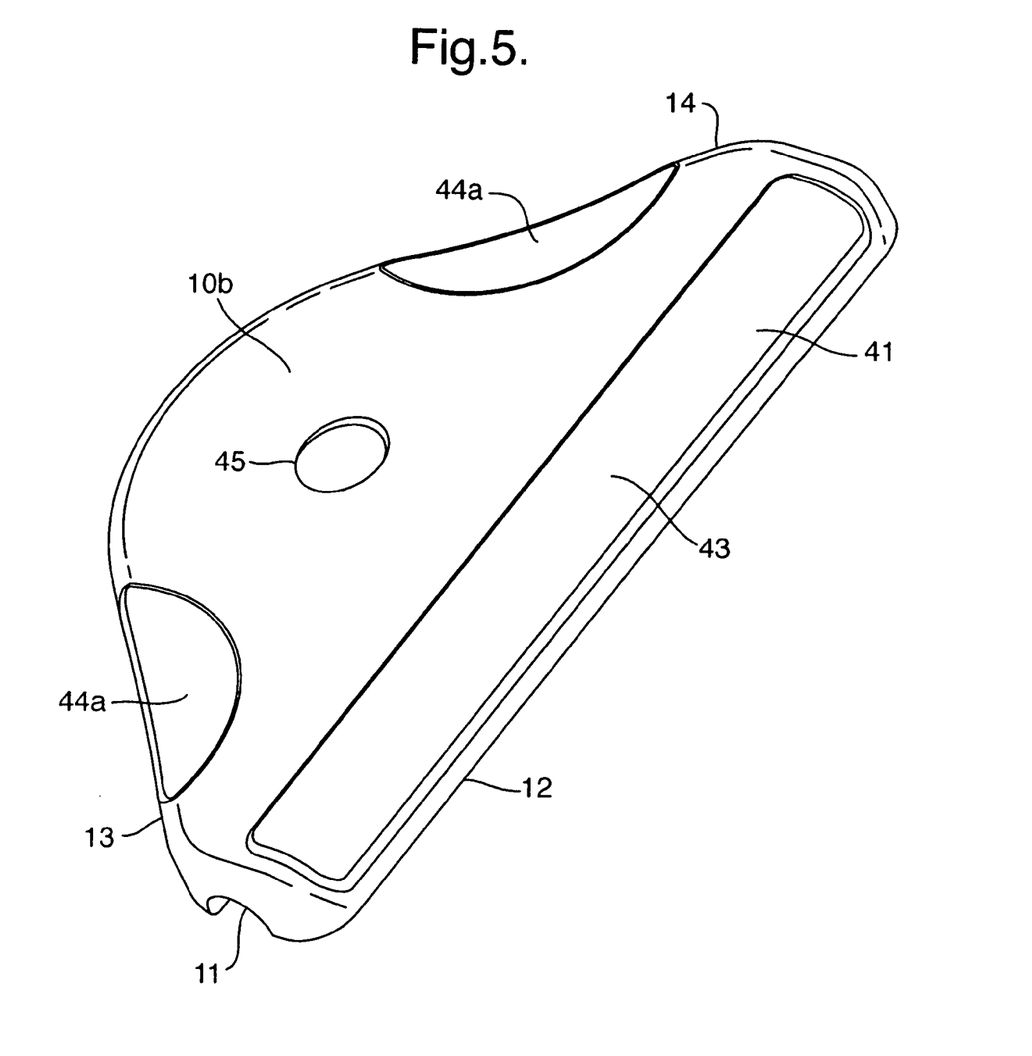
FIG. 5 is a perspective view of a further embodiment.

FIG. 5 illustrates an alternative embodiment where the abrasive surface 41 is provided by a strip of sandpaper 43 adhered to the curved long edge 12 of the underside shell 10b. The sandpaper 43 may be applied to a shallow recess, to help locate the sandpaper 43 on the housing 10. In other embodiments (not shown) the sandpaper 43 may be applied to the whole of the semi-cylindrical profile of the long edge 12.

In another embodiment (not illustrated) the abrasive surface 41 may be provided by applying an abrasive coating to a region of the housing 10, such as the semi-cylindrical long edge 12. This may comprise a matrix of resin that contains abrasive particles or porosity.

Tests have revealed that the abrasive surface 41 should be (or should be the equivalent of) between 280-800 grit sandpaper, most preferably around 400 grit.

The maternal-skin electrode 15 is adapted to be removed easily from the housing 10, in order to allow the abrasive surface 41 to be rubbed against the mother's skin without obstruction. The connector 1 is of a shape which can be easily gripped in the hand of the user, while also providing an abrasive surface 41 that is of a length corresponding substantially to the diameter of the maternal-skin electrode 15.

Hollows 44a are provided in the housing 10 to improve the comfort in the hand and to provide a better grip on the housing 10. A circular hollow 44b is provided in the top shell 10a for the thumb to grip into when rubbing the abrasive surface 41 against the mother's skin. This circular hollow 44b also provides a guide to the midwife when fitting the circular maternal-skin electrode 15, allowing the contact portion 40 to be lined up easily with the centre of the circular hollow 44b and the opening 45. The internal surface 8 of the top shell 10a is provided with a socket 46 for supporting the end of the contact portion 40 which extends the third electrical contact member 34.

Figure 2B:
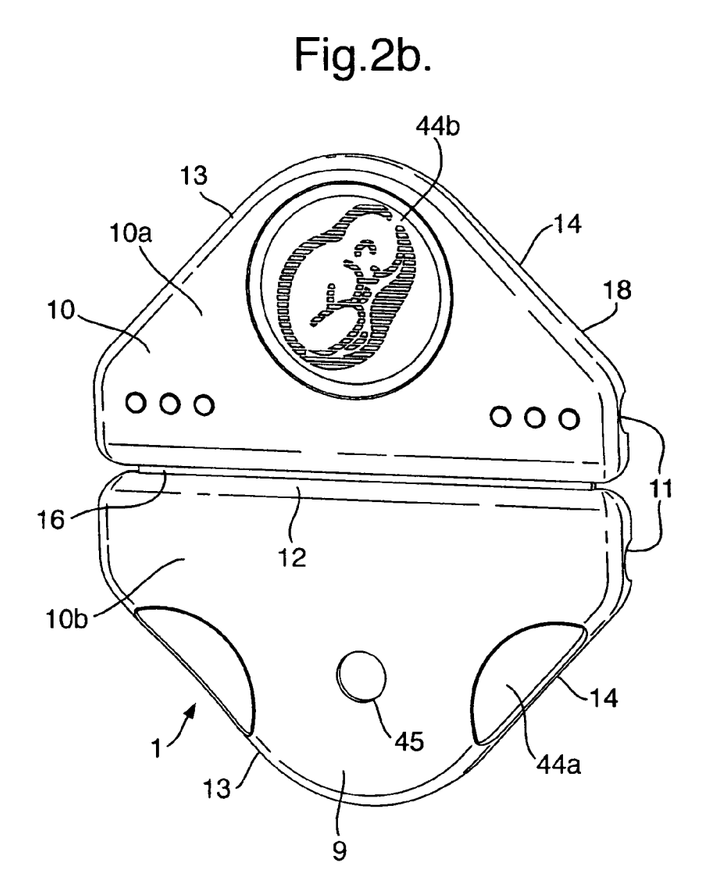

As shown in FIG. 5, while it is preferred to mould the housing 10 in a clam-shell form as illustrated in FIGS. 2a and 2b because of the manufacturing advantages, it is also possible, if desired, to mould the shells 10a and 10b as separate items and then join them subsequently in the manufacturing process to obtain the advantages of the triangular form and the abrasive surface 41.

In the present invention, the connector is intended to be used only once and then disposed of, in order to prevent transmission of infectious diseases. To ensure that the single-use connection system is not re-used, the connector 1, or other component such as the plug 2 or fetal electrode, may be provided with a programmable electronic ID-device 50 (the fetal electrode plug 2 is provided with such an ID-device 50 in FIGS. 6a and 6b, and in FIG. 8, the connector plug 60 is provided with an ID-device 50), in order to guarantee single-use and to ensure the components are only used with approved products. The ID-device 50 is preferably an Integrated Digital Rights Management Integrated Circuit (DRMIC, or ID chip). Such products are commercially available, such as the Dallas/Maxim 1-Wire® technology, where only one extra connection or wire is needed in addition to the ground connector or wire.

Typically, the fetal monitor would recognise and tag the ID-device 50 belonging to the leg-plate connector 1, fetal electrode plug 2, connector plug 60, fetal electrode or other components, with details such as the date and time of first connection. The fetal monitor may also check to make sure the component is an approved device. For example, the set of components may comprise an individual product number that must match for the set to work. The fetal monitor then accepts this tagged component for a limited amount of time only.

With the same technique, it is also possible to reject expired electrodes as the batch number, date of production or sterilisation, may be initially stored on the ID-device 50. To maximise the fECG signal quality, the monitor can also be set up to only accept safe electrodes or other component of the highest quality, or to only perform sensitive analysis on fECG signals recorded with electrodes with a conforming intended use.

The ID-devices 50 are available in a small diameter, for example, less than 4 mm, and so are small enough to be placed in the cylindrical hub of a fetal scalp electrode. The ID-device 50 could also be placed in the tip of the fetal electrode plug 2, with the diameter of the plug 2 still being sufficiently small to fit within a drive tube that is used to apply the fetal electrode to the scalp of the fetus. In this way, the drive tube can still be retracted over the plug 2 once the scalp electrode has been fitted.

Figure 6A:
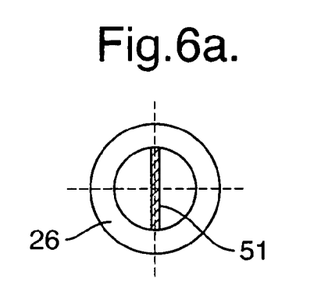
FIGS. 6a and 6b are schematic representations of the plug tip and fetal electrode plug in section in accordance with a further embodiment.
Figure 6B:
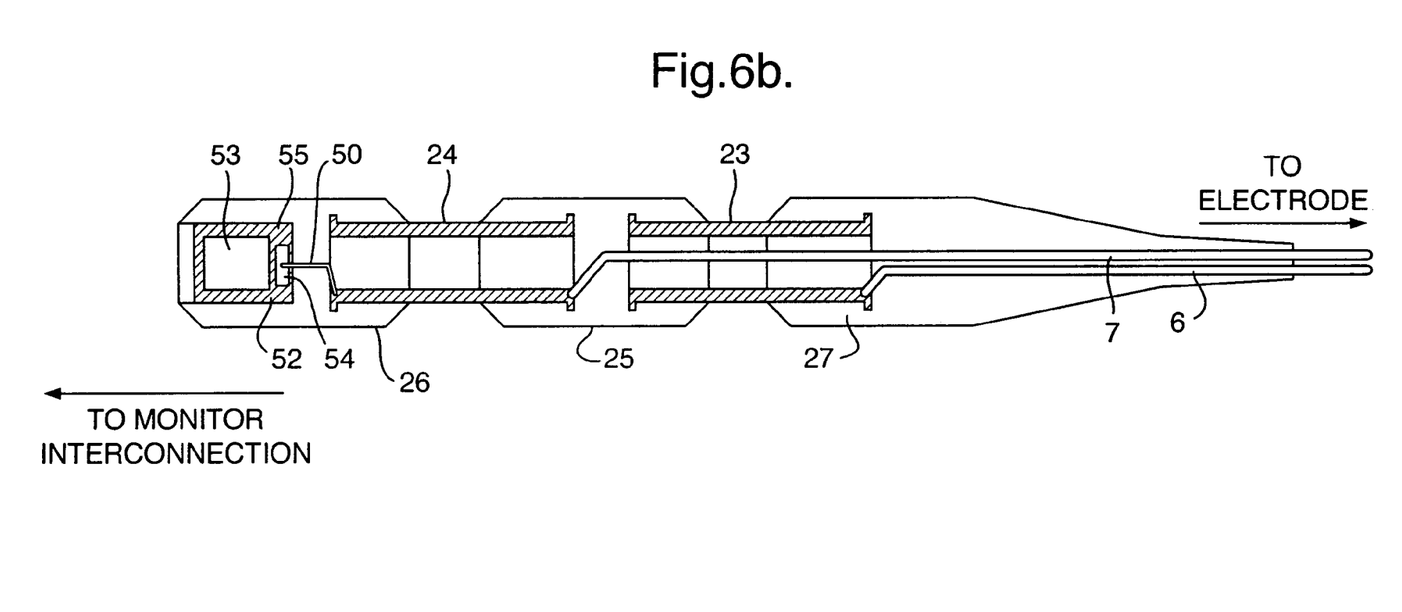

As the connection of an ID-device 50 within a leg-plate connector 1 is straightforward (the ID-device 50 can be located anywhere within the housing 10 of connector 1 and preferably uses solderless connection to a contact member), instead an example of an embodiment where an ID-device 50 is placed within the plug 2 of the fetal electrode, is shown with reference to FIGS. 6a and 6b.

The ID-device 50 is integrated into the plug tip 26 as shown in FIGS. 6a and 6b. The conductive side 51 of printed circuit board 52 is used as a third plug terminal, for contact with an additional centred contact member (not shown) for 1-wire communication in the leg-plate connector 1. The printed circuit board 52 is approximately 2.5×3.6 mm and holds the ID-chip 53, which is approximately 1.9×2.6 mm, and solder pad 54 for connection to the signal ground terminal member 55. The plug terminals 51, 24, and 23 are all recessed below the level of the plug body 26, 25, 27, to conform to International regulatory safety standards, e.g. IEC 60601-1 with regards to touch-proof connectors. Overall, the plug 2 is similar in appearance to a 3.5 mm stereo plug.

One risk is that cable faults may lead to higher currents than expected by International regulatory safety standards, when communication is made by the fetal monitor with the ID-device. This is really only a problem in the case where the ID-chip is placed in the plug tip 26, or in another position close to the fetal electrode. To overcome this problem, the fetal monitor should be equipped with a low current impedance sensing network on the monitor wires, in order to identify such a cable fault prior to any communication with the ID-device.

Figure 7:
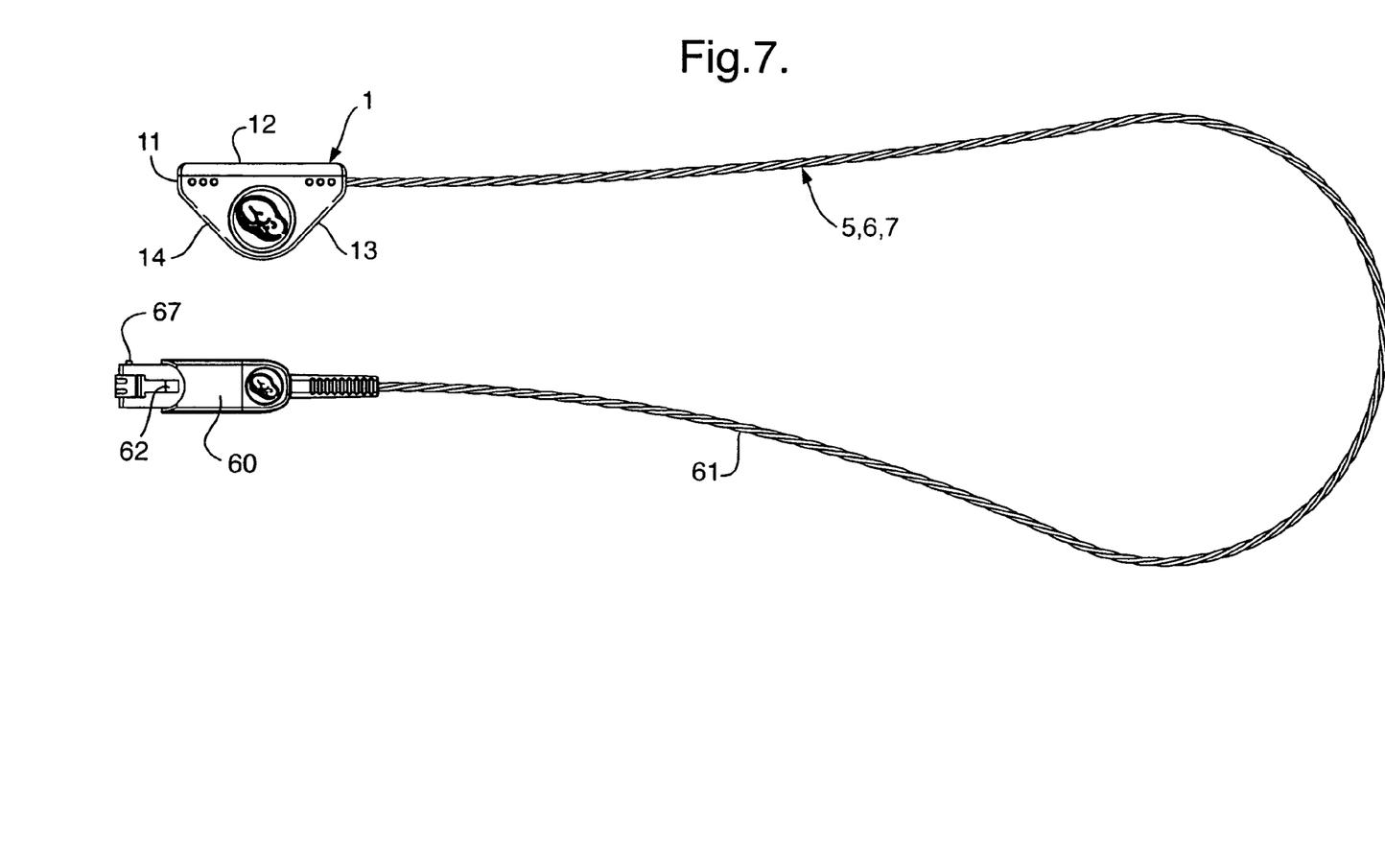
FIG. 7 is a perspective view of a preferred connector, including non-removable leads and a plug.

FIG. 7 illustrates a perspective view of a preferred embodiment of the leg-plate connector 1, including a non-removable cable 61 comprising electrical leads 5, 6, 7. The cable 61 exits the connector 1 from a corner opposite to the fetal electrode plug socket 11 and terminates at a connector plug 60. The connector 1, cable 61 and connector plug 60 cannot be disassembled.

The connector plug 60 could be of any format, and could be either a male or female connector, but most preferably is a male RJ-45 type connector as shown, since these are not particularly expensive. The connector plug 60 has a lever 62 which can be pivoted about spindle 63 when pressed in order to release the plug 60 from a corresponding female connector 64 provided in the fetal monitor or an intermediate component (see FIG. 8). On the other side of the connector plug 60 to the lever 62, a series of eight contact pins 65 are provided to make electrical contact with the corresponding contacts of the female connector 64. The grooves 66 housing these contact pins 65 can be seen in FIGS. 9a and 9b, which illustrate another embodiment of the connector plug 60 with the same RJ-45 pin arrangement.

Figure 8:
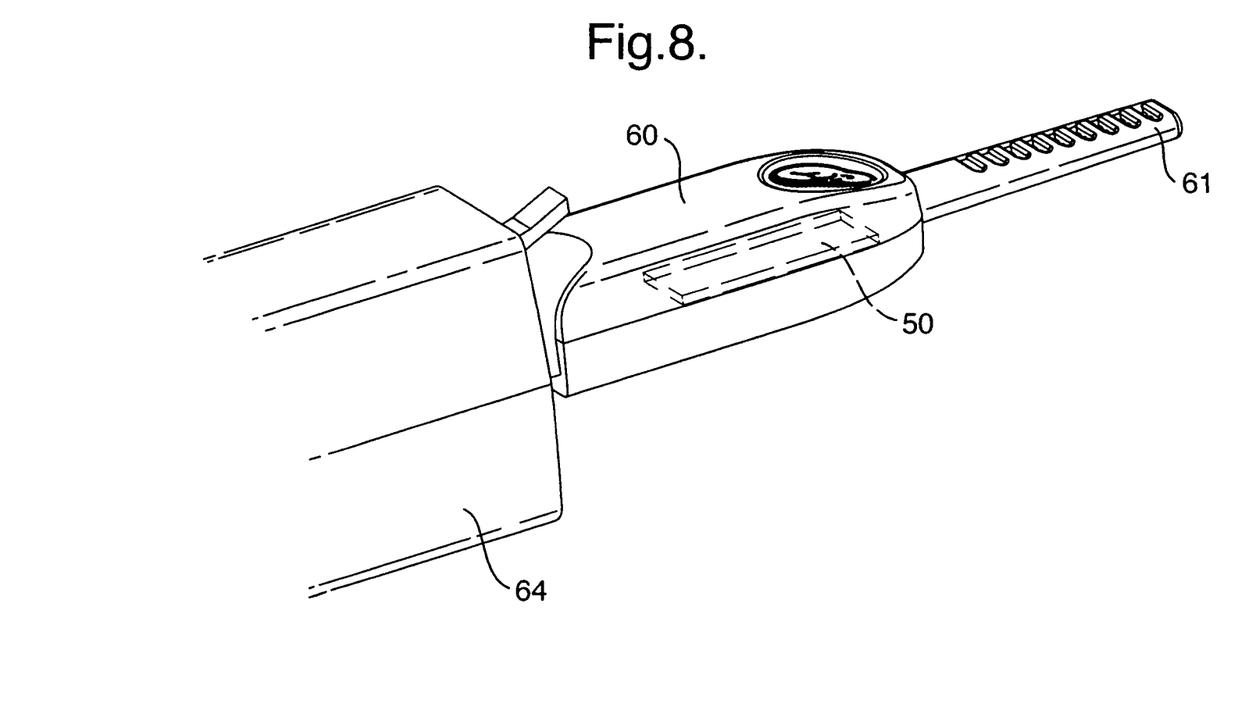
FIG. 8 is a perspective view of a preferred connector plug which has been fitted with an ID-device.
Figure 9A:
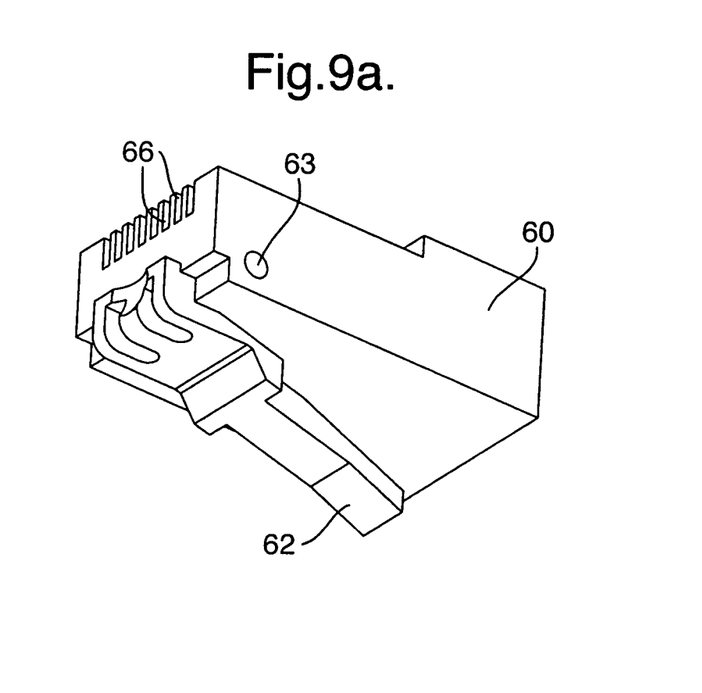
FIGS. 9a and 9b show perspective views from different angles of another preferred connector plug.

As can be seen in FIG. 8, the connector plug 60 is provided internally with an ID-device 50 in the form of a printed circuit board having, for example, dimensions of 7×18×0.8 mm and including an ID-chip. The ID-device 50 operates to ensure that the connector 1, which is permanently attached to the connector plug 60, can only used for one patient, for example, by permitting the assembly of the leg-plate connector 1, cable 61 and connector plug 60 to be used only for a specified period of time.

Figure 9B:
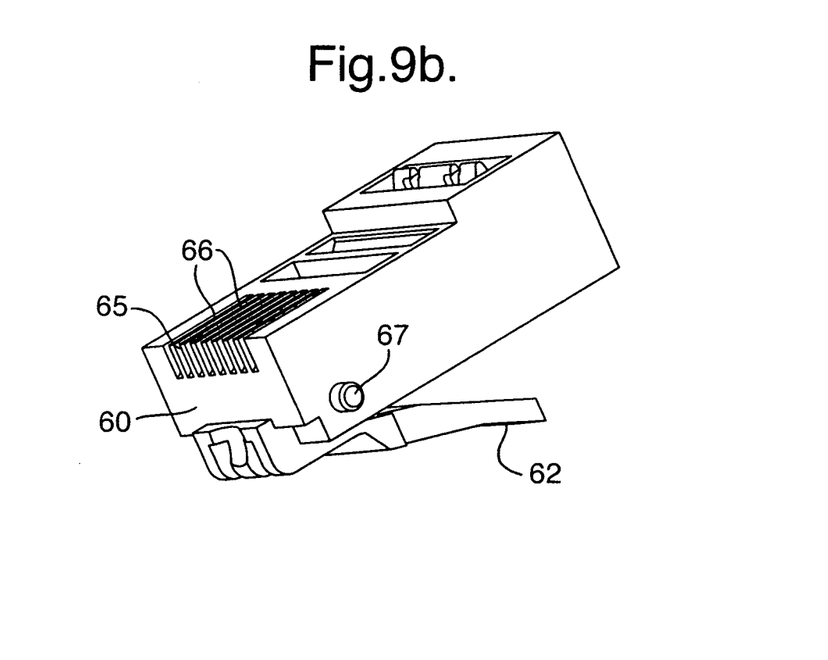

While it is preferred to use a connector plug which is of an RJ-45 format because of the cost benefits associated with such a common format, a problem arises because it must be ensured that the connector plug 60 cannot be inadvertently connected to some other network device. If this were to happen then there is a possible risk of an electric shock to the mother or fetus. As a solution to this problem, the connector plug 60 is provided with means to prevent its insertion into a standard RJ-45 socket on some other item of equipment. As shown in FIGS. 7 and 9b, this means could comprise a pin 67, which projects out of the side of the connector plug 60 as an extension from drilled hole 63. This will block the insertion of the connector plug 60 into a socket which does not have a corresponding groove to receive the pin 67, and so will ensure that a user can only insert the connector plug 60 into a correct fetal monitor or a correct adapter for the fetal monitor. The pin 67 can easily be embedded in the connector plug 60 during the operation of crimping the plug onto the end of the cable. In this way, a low-cost standard RJ-45 plug, and all the standard and effective tools available for the manufacturing can be used to produce the unique and safe connector plug 60, which is both mechanically keyed to the leg-plate connector 1 and electronically locked to prevent multiple use.

Figure 9C:
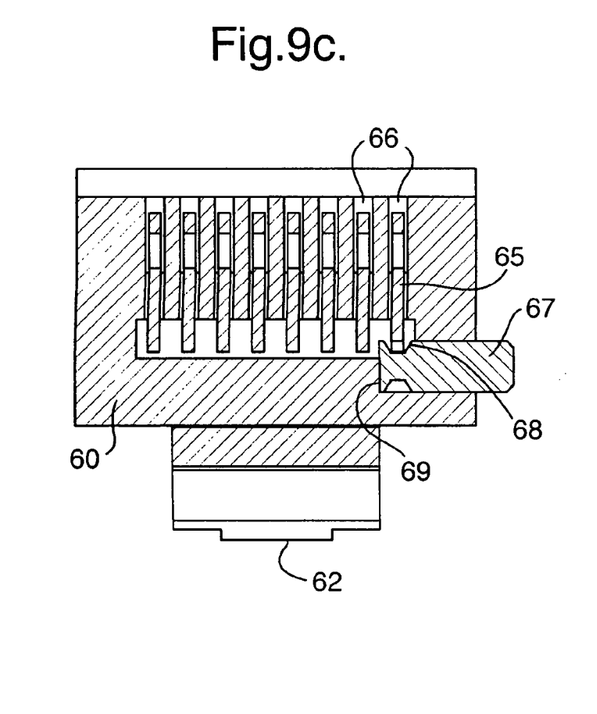
FIG. 9c is a cross-sectional view of the preferred connector plug taken along line A-A in the side view of FIG. 9d.
Figure 9D:
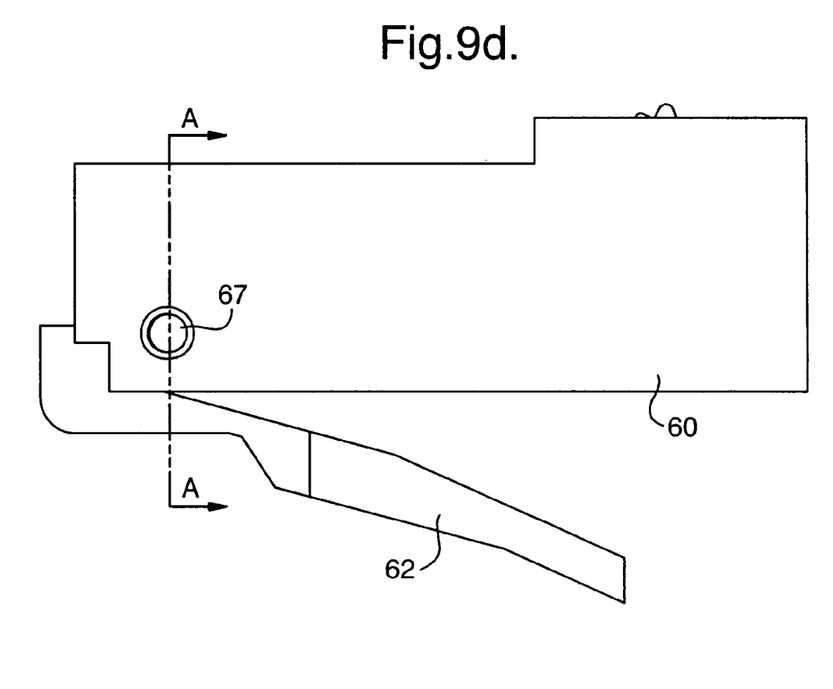

FIG. 9d shows a side view of connector plug 60 with the pin 67. FIG. 9c is a cross-sectional view through the connector plug 60 along line A-A. As can be seen in FIG. 9c, the pin 67 includes a recess 68 in the form of a circumferential groove at the end 69 of the pin 67 that is retained within a hole 63 drilled in the connector plug 60. During the operation of crimping the connector plug 60 onto the end of the cable 61, a contact pin 65 is crimped so as to project into the recess 68 and thereby lock the pin 67 in place projecting from the side of the connector plug 60. This makes for a simple manufacturing process as the connector plug 60 can be modified with the pin 67 during the single crimping process.

Although the invention above has been described in connection with preferred embodiments of the invention, it will be evident for a person skilled in the art that several modifications are conceivable without departing from the invention as defined by the following claims.

What is claimed is:

1. A single-use connector for a fetal electrode, the connector comprising:
    a housing having a first socket for receiving a plug of a fetal electrode;
    two or more contacts arranged within the first socket for receiving electrical signals from the plug when it is inserted;
    a second socket for a maternal reference electrode provided on an underside of the housing,
    wherein the housing is made from a moulded body which has a clam-shell form, the housing comprising two shells of substantially rigid material providing, in use, the underside and a top surface of the housing respectively, where each shell is integrally connected to the other along a common straight portion of edge.

2. The connector as claimed in claim 1 wherein the shells of the housing are substantially triangular in outline.

3. The connector as claimed in claim 2, wherein each shell has a substantially right angle triangular outline, having one long edge and two shorter edges.

4. The connector as claimed in claim 3, wherein the shells are integrally connected by a hinge along the long edge and welded together along the short edges.

5. The connector as claimed in claim 1, wherein the connector includes an abrasive surface for abrading skin prior to attachment of the maternal reference electrode.

6. The connector as claimed in claim 5, wherein the abrasive surface comprises a series of projections which are integral with the housing.

7. The connector as claimed in claim 5, wherein the abrasive surface is a strip of sand-paper.

8. The connector as claimed in claim 5, wherein the abrasive surface is provided on an edge of the housing.

9. The connector as claimed in claim 1, wherein two contacts of the first socket are provided by first and second contact members, and a connection to a maternal reference electrode is provided by a third contact member, wherein the first, second and third contact members share the same base geometry.

10. The connector as claimed in claim 1, wherein the connector is fitted with a programmable electronic ID-device that is adapted to prevent re-use of the connector.

11. The connector assembly comprising a connector as claimed in claim 1, a cable extending from the connector which comprises leads for conveying electrical signals from the connector to a fetal monitor, the cable terminating in a connector plug, wherein the connector plug contains a programmable electronic ID-device that is adapted to prevent re-use of the connector.

12. A method of making a single-use connector for a fetal electrode comprising the steps of:
    moulding a housing of the connector by providing material between opposed die faces of a moulding apparatus, the housing being moulded in an open configuration where one die face provides the internal surface profile of the housing and the other die face provides the external surface profile of the housing, whereby the moulded housing has a clam-shell form comprising two shells of substantially rigid material that are integrally connected along a common straight portion of edge which hinges the shells together;
    closing the moulded housing so that a remainder of the edges of the shells are brought together; and
    fastening the shells together to retain the shells in a closed configuration.

13. The method as claimed in claim 12, wherein the step of providing material between opposed die faces includes placing a square or rectangular blank of material between the die faces, and wherein the shells are moulded to provided the internal and external surface profiles with the common straight portion of edge extending along a diagonal of the blank.

14. The method as claimed in claim 12, wherein the step of fastening the shells together includes the step of welding a remainder of the edge of one shell to a remainder of the edge of the other shell.

15. The method as claimed in claim 12, wherein the method includes the step of forming an abrasive surface on the housing.

16. The method as claimed in claim 12 including the steps of:
    providing the connector with a cable comprising electrical leads for conveying electrical signals to a fetal monitor, and fixing one end of the cable to the connector by attachment to a set of contact members that are retained within the connector housing,
    attaching a connector plug to the other end of the cable, the connector plug including a programmable electronic ID-device which is adapted to prevent re-use of the connector.

* * * * *